(12) United States Patent
Kroll

(10) Patent No.: US 6,820,619 B2
(45) Date of Patent: *Nov. 23, 2004

(54) ALTITUDE ADJUSTMENT METHOD AND APPARATUS

(75) Inventor: Mark W. Kroll, Simi Valley, CA (US)

(73) Assignee: Kroll Family Trust ( * ) Notice: Subject to any disclaimer, the term of this patent is extended or adjusted under 35 U.S.C. 154(b) by 0 days.

This patent is subject to a terminal disclaimer.

(21) Appl. No.: 10/435,275

(22) Filed: May 9, 2003

(65) Prior Publication Data

US 2004/0003815 A1 Jan. 8, 2004

Related U.S. Application Data

(63) Continuation-in-part of application No. 09/447,323, filed on Nov. 22, 1999, now Pat. No. 6,561,185, which is a continuation-in-part of application No. 08/927,242, filed on Sep. 11, 1997, now Pat. No. 5,988,161.

(51) Int. Cl.⁷ ............................ A62B 7/00; A61M 16/00
(52) U.S. Cl. .............................. 128/205.11; 128/205.27; 128/205.28; 128/204.22
(58) Field of Search ....................... 128/202.12, 203.25, 128/205.11, 205.25, 205.26, 205.27, 205.28, 204.22, 206.15, 914, 910

(56) References Cited

U.S. PATENT DOCUMENTS

| | | | | |
|---|---|---|---|---|
| 4,086,923 A | | 5/1978 | Henkin | |
| 4,232,667 A | * | 11/1980 | Chalon et al. | 128/203.26 |
| 4,586,500 A | * | 5/1986 | Glynn | 128/204.15 |
| 5,444,762 A | | 8/1995 | Frey et al. | |
| 5,512,908 A | | 4/1996 | Herrick | |
| 5,625,364 A | | 4/1997 | Herrick et al. | |
| 5,670,742 A | | 9/1997 | Jones | |
| 5,678,200 A | | 10/1997 | Levi | |
| 5,684,861 A | | 11/1997 | Lewis et al. | |
| 5,850,833 A | * | 12/1998 | Kotliar | 128/202.12 |
| 5,856,803 A | | 1/1999 | Pevler | |
| 5,873,040 A | | 2/1999 | Dunn | |
| 5,877,630 A | | 3/1999 | Kraz | |
| 5,924,418 A | * | 7/1999 | Lewis | 128/204.22 |
| 6,561,185 B1 | * | 5/2003 | Kroll | 128/202.12 |

FOREIGN PATENT DOCUMENTS

WO WO 97/10020 * 3/1997

* cited by examiner

Primary Examiner—Henry Bennett
Assistant Examiner—Mital Patel

(57) ABSTRACT

A portable method and apparatus for allowing an individual to pre-adjust at sea level for future high altitudes is taught. The invention teaches the use of a small portable breathing gas control system to adjust the gas concentrations going to a subject's face mask.

13 Claims, 7 Drawing Sheets

ALTITUDE ADJUSTMENT METHOD AND APPARATUS

This application is a continuation-in-part of U.S. Ser. No. 09/447,323 filed Nov. 22, 1999 now U.S. Pat. No. 6,561,185 which was a continuation-in-part of U.S. Ser. No. 08/927,242 filed Sep. 11, 1997, now U.S. Pat. No. 5,988,161 which is included, by reference, in its entirety.

BACKGROUND OF THE INVENTION

Altitude sickness strikes thousands of individuals every year resulting in problems from sleep disorders to pulmonary edemas to death. These individuals are skiers, mountain climbers, or merely business travelers to high altitude regions. The key to dealing with the altitude sickness is taking advantage of the body's ability to gradually acclimatize through a transition through progressively higher altitudes.

Unfortunately, most individuals do not have the time to acclimatize. For example, and individual flying to a high ski hill will typically spend a few hours of flying and driving to be at the ski hill thus depriving the body of the opportunity to acclimatize.

The physiology of altitude sickness and the adjustment to altitude is covered in numerous textbooks. An excellent one is "Medicine For Mountaineering" by James Wilkerson, M.D. (copyright 1992, published by The Mountaineers of Seattle, Wash.) from which the immediately following discussion is liberally taken.

The body adjusts to altitude by increasing respiratory volume, increasing the pulmonary artery pressure, increasing the cardiac output, increasing the number of red blood cells, increasing the oxygen carrying capability of the red blood cells, and even changing body tissues to promote normal function at lower oxygen levels.

At an altitude level of 3,000 feet the body already begins increasing the depth and rate of respiration. As a result of this more oxygen is delivered to the lungs.

In addition, the pulmonary artery pressure is increased which opens up portions of the lung which are normally not used, thus increasing the capacity of the lungs to absorb oxygen. For the first week or so, the cardiac output increases to increase the level of oxygen delivered to the tissues. However, that particular adjustment fades after the first week.

The body also begins to increase the production of red blood cells. Other changes include the increase of an enzyme (DPG) which facilitates the release of oxygen from the blood and increase the numbers of capillaries within the muscle to better facilitate the exchange of blood with the muscle.

About 80% of the adaptation is finished by 10 days.

Slowly increasing the altitude from sea level to the target altitude appears to be the best solution.

The most difficult time for altitude sickness sufferers is evening when the primary function is sleeping. This is most likely due to the fact that the breathing rate decreases during sleep and thus the coping mechanism of increased respiratory rate is somewhat thwarted.

Gamow (U.S. Pat. No. 5,398,678) teaches a portable chamber to facilitate the function of an individual at higher altitudes by increasing the pressure within the chamber above that of the ambient. Lane (U.S. Pat. No. 5,101,819) teaches a method of introducing nitrogen into a flight training hypobaric chamber to simulate the lower oxygen concentrations at higher altitudes for fighter pilots.

The inventor is not aware of any other art that discusses the use of a portable device for helping an individual to adjust to altitudes.

DETAILED DESCRIPTION

Figure 1:
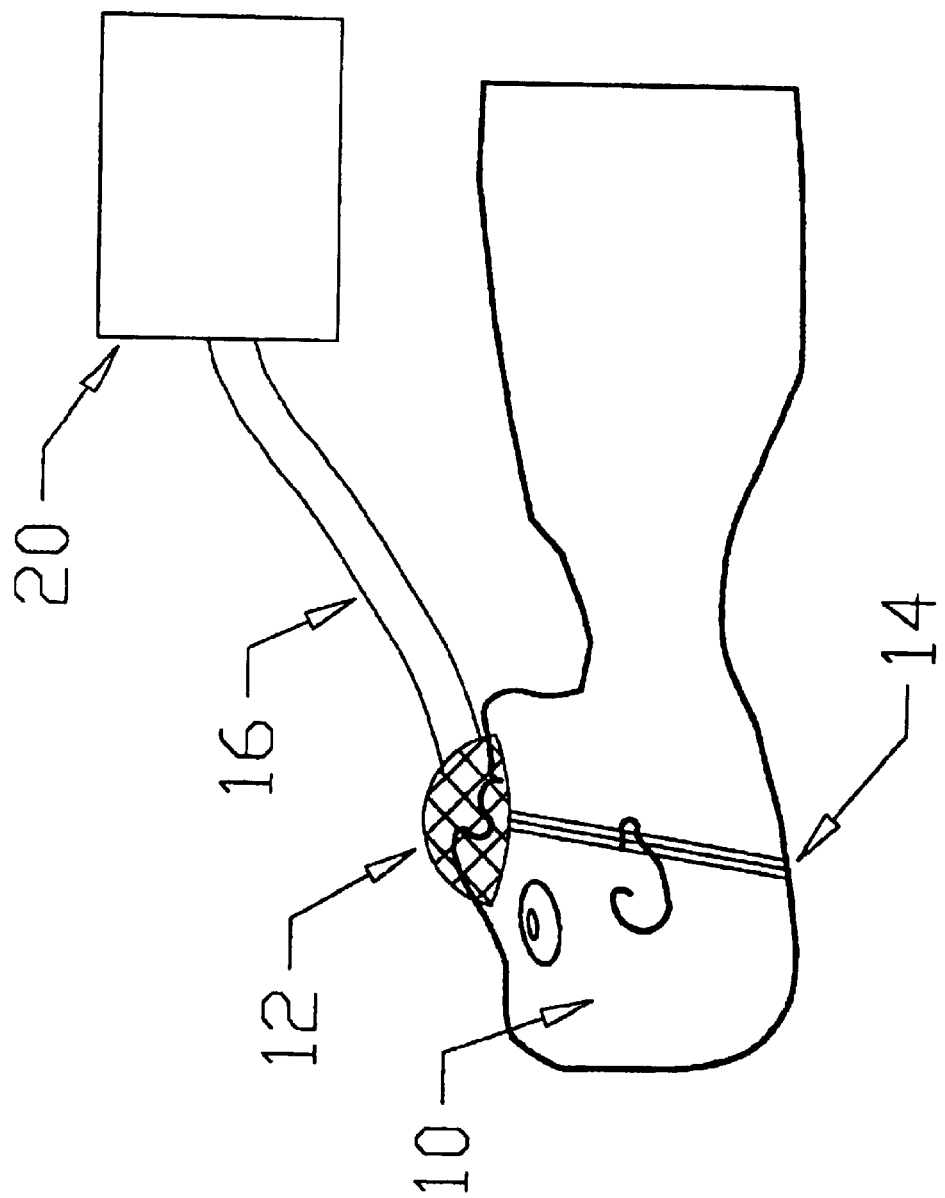
FIG. 1 shows a subject at rest using the device.

FIG. 1 shows a subject 10 using the device with mask 12 over the nose and mouth secured around the head by strap 14. The mask communicates with the main exchange unit 20 through hose 16. For convenience, hose 16 should be long enough so that the exchange unit 20 can be far enough away from the patients so that it does not interfere with their sleep. However, for optimal performance in air mixing, the hose could be made shorter to allow for more shallow breaths for the appropriate gas levels. Alternatively, the exchange unit could be made very small and built into the mask thus obviating the hose 16.

Figure 2:
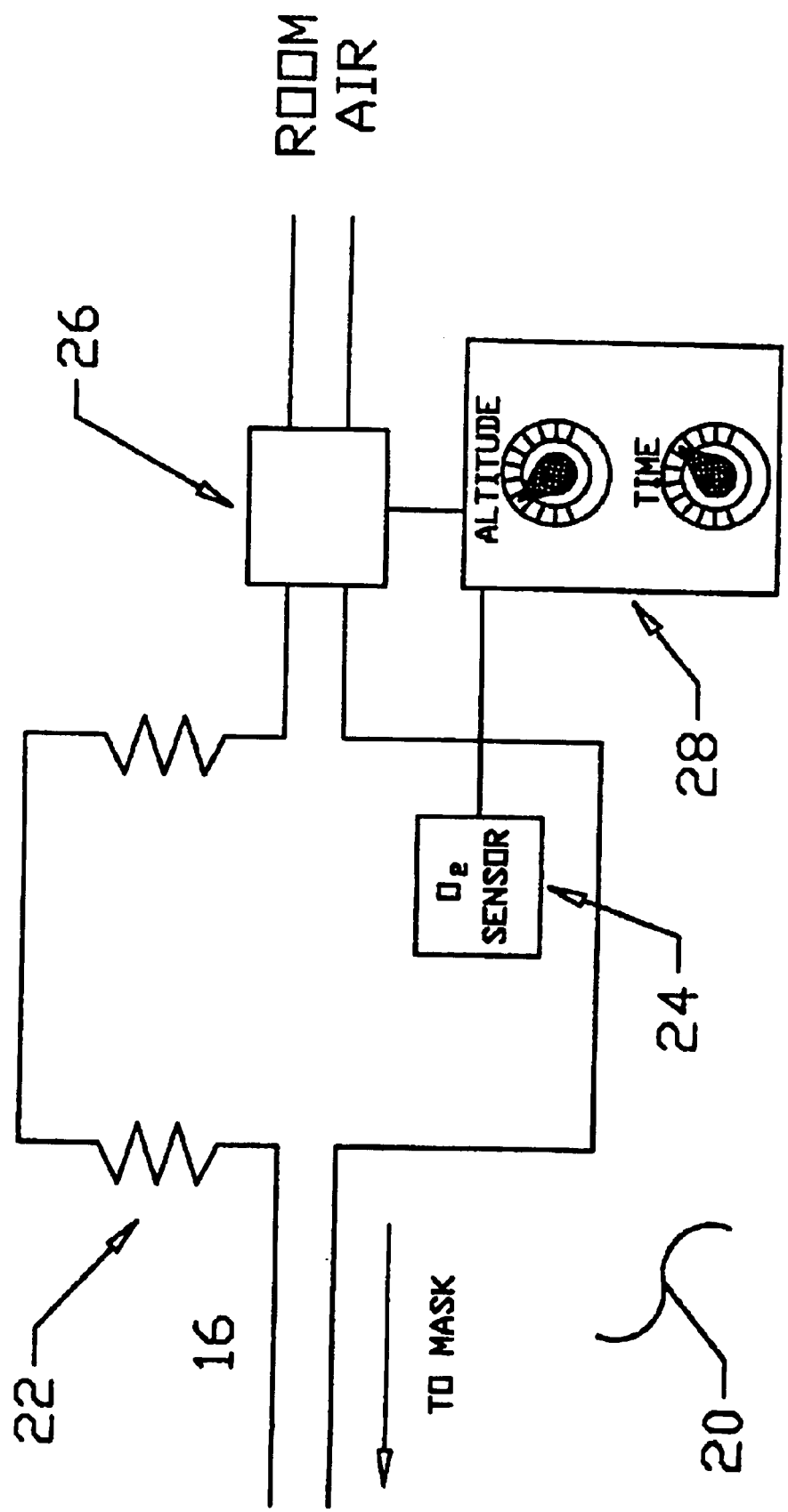
FIG. 2 shows a simple embodiment of the device.

FIG. 2 shows the details of the exchange unit 20 beginning with the hose 16 going to the mask. Flexible sides 22 allow for the chamber to expand and contract. Alternatively, flexibility could be gained by the use of elastic polymers or other materials for the unit surfaces.

Oxygen sensor 24 sits inside the chamber and feeds its signal to a control unit 28. The control unit 28 has a setting for an altitude and time. The control unit then controls the room air solenoid 26 to allow the passage of room air into the exchange unit when necessary.

The basic operation is rather straightforward. The oxygen sensor monitors the oxygen and controls the room air solenoid. The solenoid would be open or closed depending upon whether the internal oxygen level is a that appropriate level desired for the altitude simulation.

More details of this are given in the discussion of the methods which are following.

Figure 3:
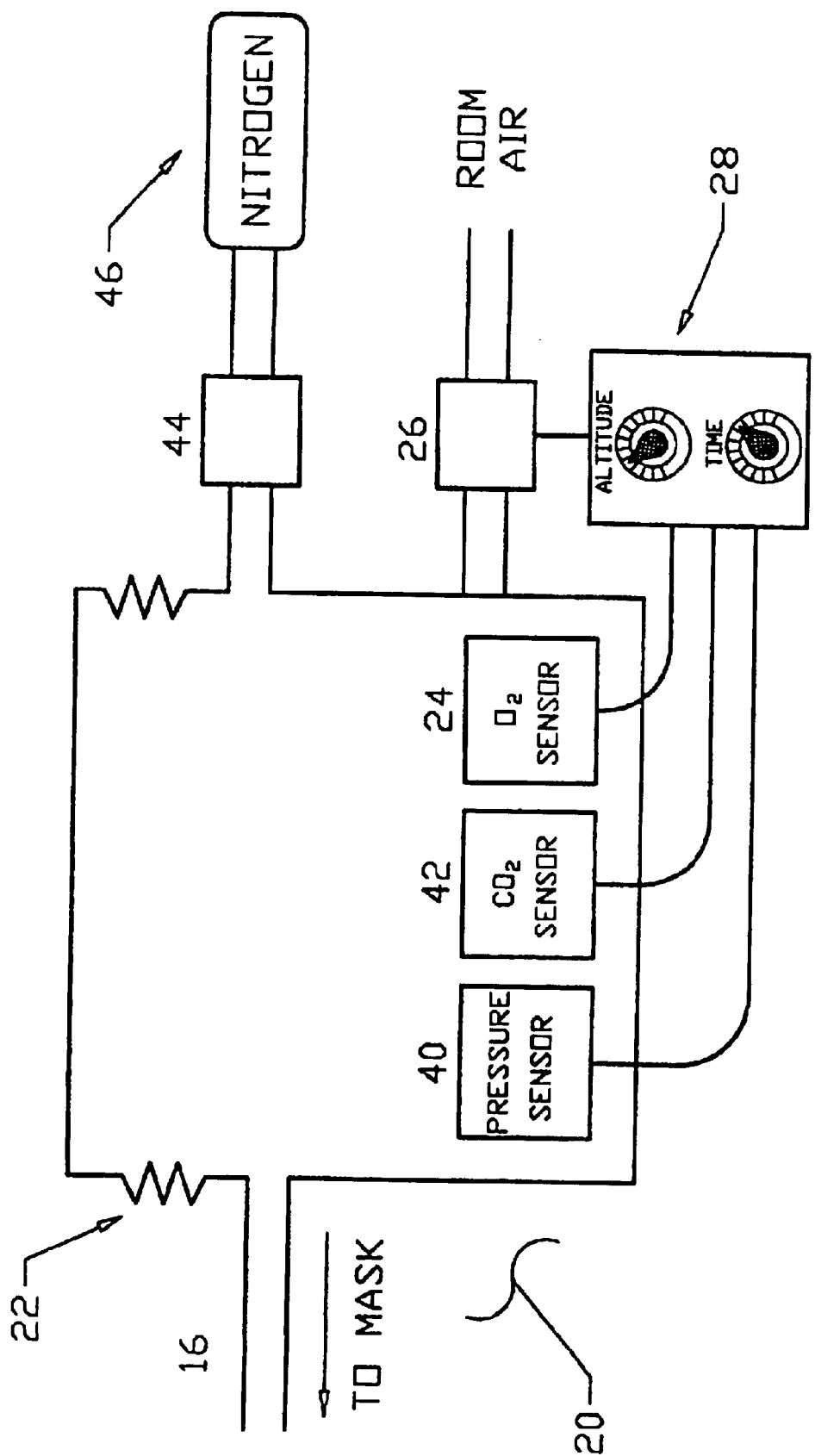
FIG. 3 shows a more complex embodiment of the device.

FIG. 3 shows a more complex embodiment of the invention which adds a pressure sensor 40 and Co2 (carbon dioxide) sensor 42 which again feed into the control unit 28. This allows for the adjustment of not only the oxygen level but the Co2 level. It maybe important, for some individuals, to minimize the level of Co2 as high levels of Co2 can interfere with breathing reflex.

A second solenoid 44 is used to allow the passage of nitrogen from a tank 46 into the chamber. This allows the reduction of oxygen levels in the chamber without merely increasing the levels of Co2 as occurs with the simpler embodiment shown in FIG. 2. This further discussion of the use of this is covered in the following method discussions of FIGS. 4 and 5.

Figure 4:
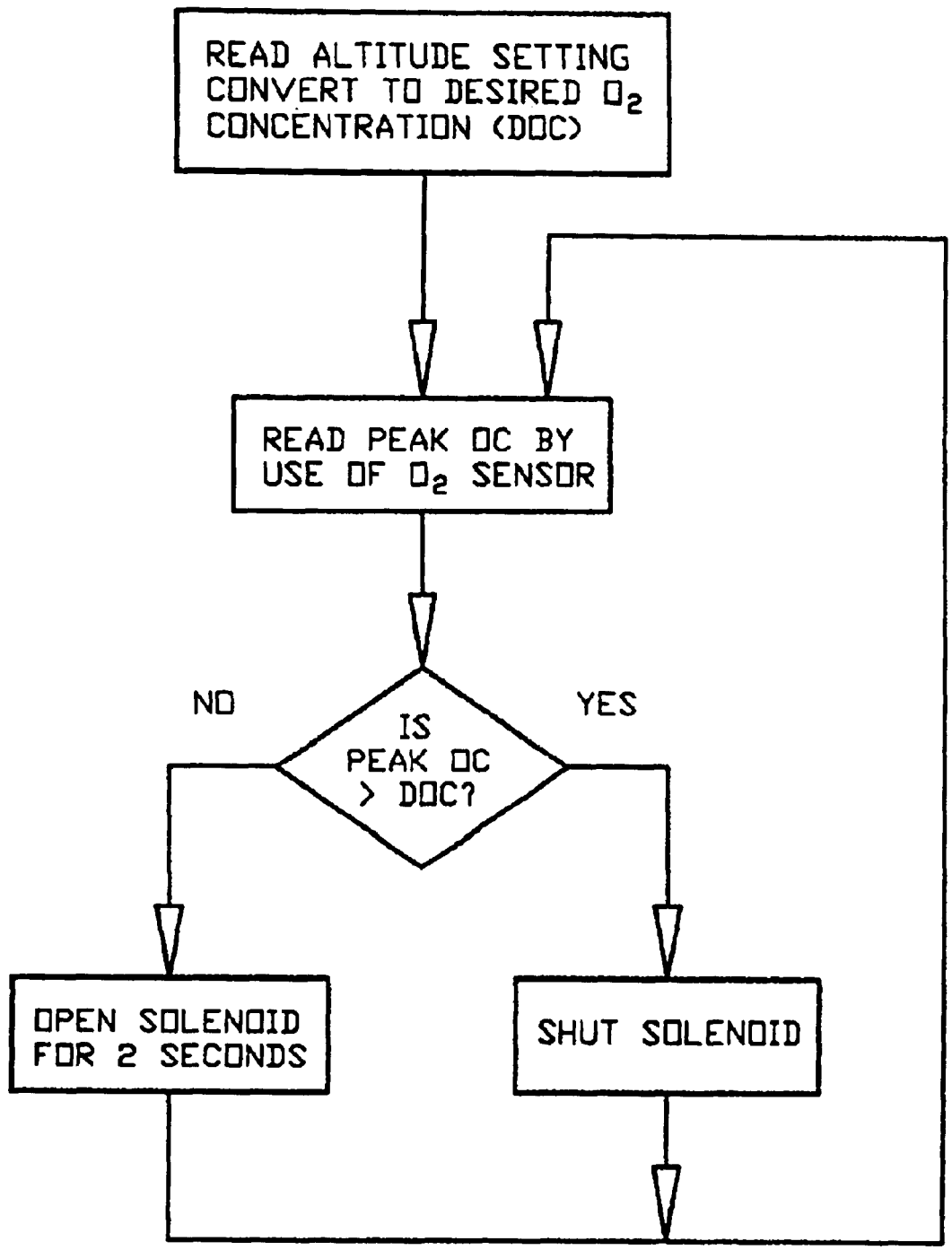
FIG. 4 shows a method of a simple embodiment.

FIG. 4 shows the method for a simple embodiment of this invention. The first step is to read the altitude setting on the control unit and to convert that to a desired oxygen level. The peak oxygen concentration is read by the O2 sensor. This should occur just before inspiration as the expired air has significantly lower levels of oxygen. If the peak oxygen concentration (OC) is greater than the desired oxygen concentration (DOC) then the solenoid remains shut. This will increase the level of carbon dioxide in the gas chamber and decrease the level oxygen.

If, in the alternative, the peak oxygen level is less than the desired oxygen concentration then the room air solenoid is open for two seconds to allow fresh air into the chamber to increase the oxygen concentration.

Figure 5:
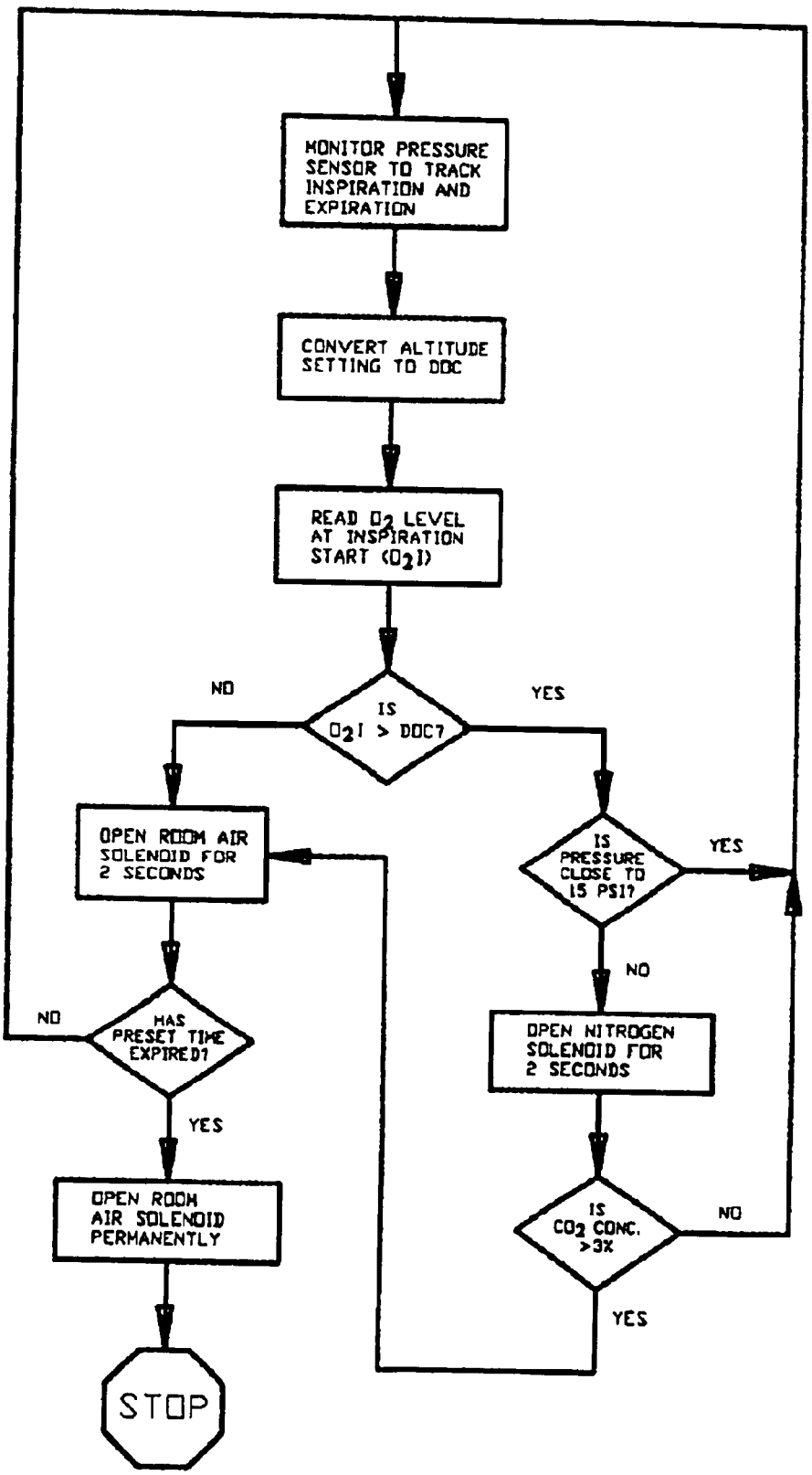
FIG. 5 shows a method for a more complex embodiment of the invention.

FIG. 5 shows a more complex embodiment of the invention. The pressure sensor is continually monitored to track inspiration and expiration. This is due to the fact that the inspiration will reduce the pressure in the tank while the expiration will increase it. Thus the control unit is continuously "aware" of the stage of breathing.

As before, the desired altitude setting is converted to a desired oxygen concentration (DOC). At the beginning of every breathing cycle (or the start of inspiration) the oxygen level is peak in the exchange box. This is referred to as the "O2I". If the O2I is greater than the desired oxygen concentration then the method examines the pressure in the box. If the pressure is close to 15 PSI (pounds per square inch—or normal atmospheric pressure) then this means the box has normal pressure and there is plenty of oxygen so the unit just goes back to monitoring. Eventually, breathing will lower the level of oxygen in the box. If, however, the pressure is not near normal sea level pressure then the nitrogen solenoid is opened for two seconds to increase the gas pressure. (There is no risk of great overpressure as the mask will simply allow the excess gas to leak out around the subject's mouth and nose.) After the nitrogen solenoid has been opened for two seconds then the Co2 concentration is examined. If this is less than 3% then the method returns back to monitoring at the top of FIG. 5.

If, however, the Co2 concentration is greater than 3% then the method opens a room air solenoid for two seconds. This allows in fresh air and will decrease the Co2 concentration. The step of opening the room air solenoid for two seconds can also be reached from a negative answer to the first question. This was, "is the O2I greater than the desired oxygen concentration?" Of the answer was no then it clearly needs to open the room air solenoid to let in oxygen rich air. After this step then the timer is examined. If the preset timer has expired then the room air solenoid is opened permanently to allow the subject to have comfortable normal breathing. Otherwise the system returns to its normal steps of monitoring, etc.

Figure 6:
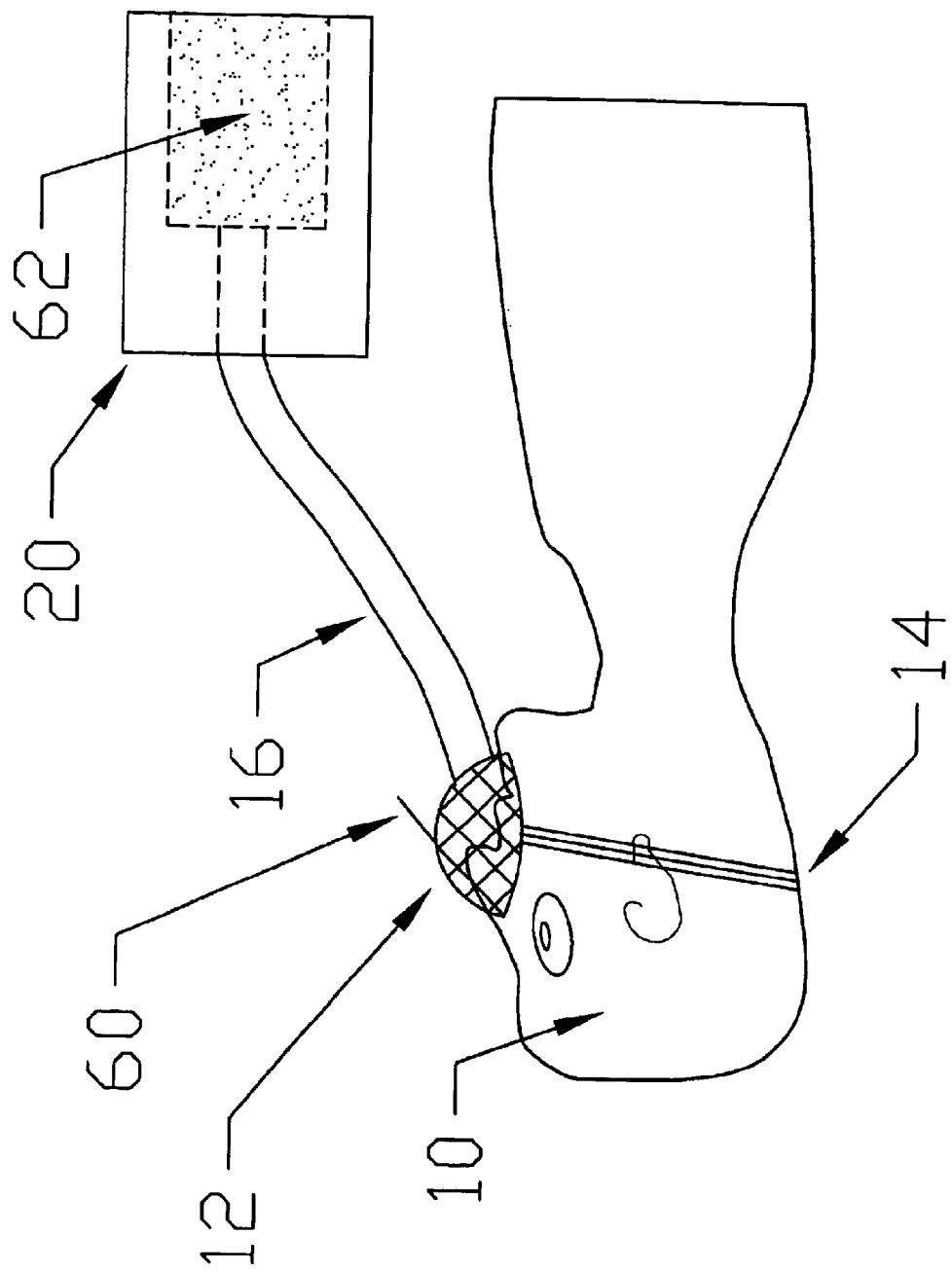
FIG. 6 shows the invention with an oxygen absorber.

An alternative preferred embodiment is shown in FIG. 6. Here flap valve 60 allows the exhaled air to go directly outside of the system. During inhalation the flap valve 60 closes forcing the breathing to take place through the exchange unit 20. Exchange unit 20 has a disposable screw-in canister 62 of an oxygen absorbent which reduces the level of oxygen in the air supplied to the user.

Typical oxygen absorbents are based on a very oxidizable metal. An excellent and inexpensive absorber is iron. This can be used very simply in the form of pellets or powder.

A feature of this invention is the use of "steel wool" for an oxygen absorber. The "wool" provides high surface area and low breathing resistance. This allows the manufacture of an inexpensive disposable cartridge for consumer use. The oxygen absorbency in increased when the iron oxidation is catalyzed. The iron performance may be improved by hydrogen reduction, electrolytic reduction, or chemical reduction.

Almost any metal can be used but none are as economical and effective as iron. Another feature of this invention is the use of dilute acetic acid (vinegar) as a catalyst for the steel wool.

Other oxygen absorbents include solid electrolyte salts, glucose oxidase. The approach of FIG. 6 is not limited to chemical oxygen absorbers. The element 62 could just as well be a package of semi-permeable membrane fibers, which preferentially leak oxygen out the sides but freely allow the passage of nitrogen. Representative membranes are composed of 4-methyl-penthene-1 with a wall thickness of 12 microns and internal diameters on the same order.

The system of FIG. 6 offers advantages of simplicity and cost of that of FIG. 2. There is no need for a valve or other controls. The canister 62 merely absorbs oxygen during the user's sleep and stops absorbing when the iron is all oxidized. At that point the canister is replaced. The canister resistance controls the flow of air and the simulated altitude of the device. Different canister geometries will simulate different altitudes.

It will be appreciated that the oxygen absorber approach could be used in conjunction with the system of FIG. 3 to replace the nitrogen source 46. Instead, room air would be filtered through the oxygen absorber to provide the nitrogen-rich and oxygen-reduced air.

Figure 7:
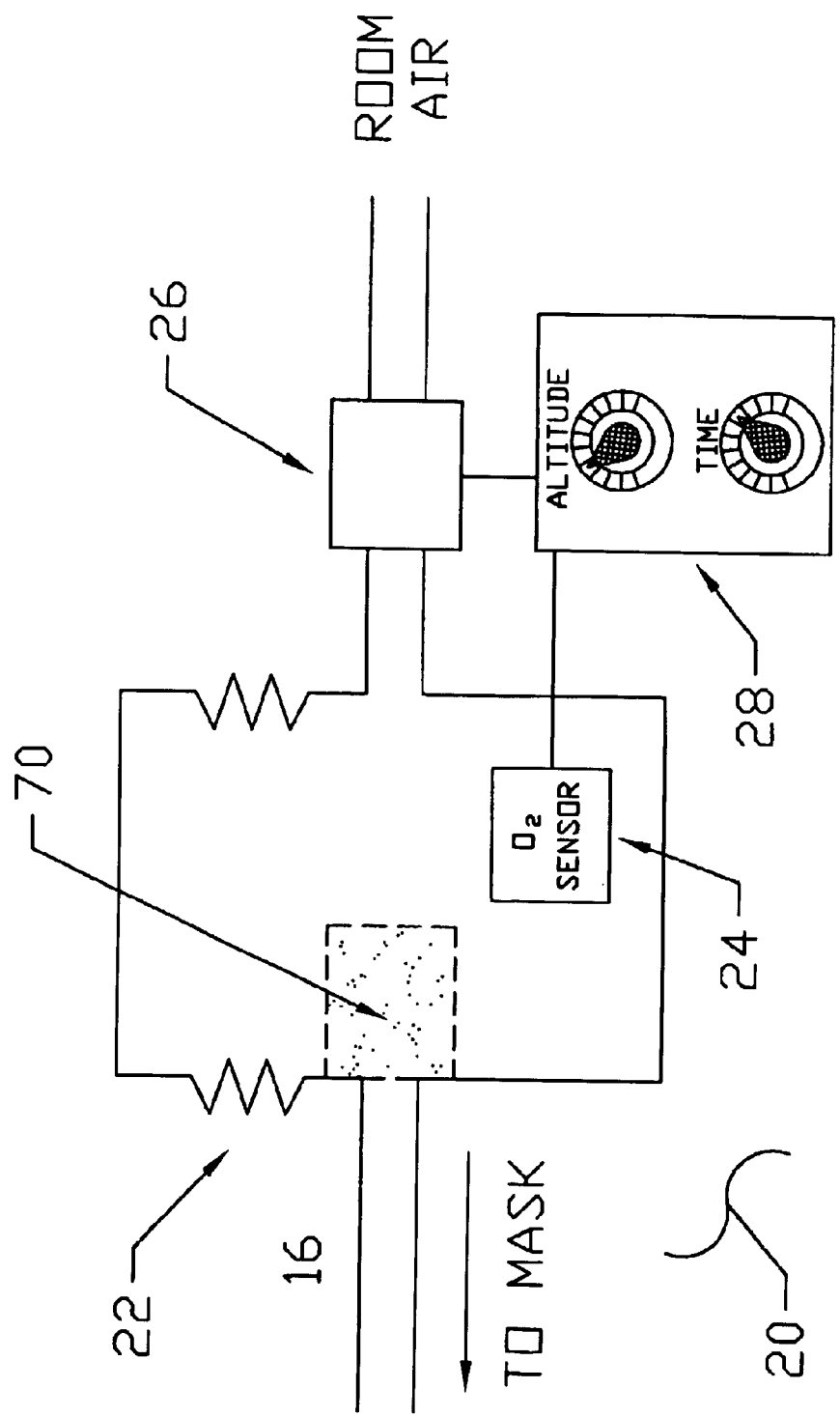
FIG. 7 shows the invention with a $CO_2$ absorber.

The device in FIG. 7 is a modification of that of FIG. 2. The modification is the addition of a disposable carbon dioxide CO2 absorber shown as element 70. While the system of FIG. 2 would work fine to lower the partial pressure of oxygen seen by the user, the increase in CO2 levels could interfere with sleep. High levels of CO2 cause increased breathing volume and eventually leads to psychological discomfort and even panic.

The O2 sensor 24 and control unit 28 may be dispensed with in this higher-value system. The geometries of the CO2 canister and the exchange chamber could be merely designed to simulate a fixed 8000 feet for optimal sleep adjustment.

It may seem paradoxical, at first blush, to attempt to lower CO2 while, at the same time, attempting to lower oxygen levels. However, by lowering both, the relative level of nitrogen is increased. This has the net effect of lowering the partial pressure of the oxygen.

There are many effective absorbers of CO2 as it is highly reactive. Any metal hydroxide works well. A very effective one is sold under the trademark "SodaSorb" by the WR Grace Company. It is a mixture of sodium-, calcium-, and potassium hydroxide. It is sometime described as being primarily sodium hydroxide and calcium oxide. (This distinction is not critical as the water vapor in the exhalant quickly converts the calcium oxide to calcium hydroxide.) The carbon dioxide reacts with the hydroxides to form carbonates. Similarly calcium bicarbonate is a very economical CO2 absorber.

Lithium hydroxide is light but more expensive. As a powder it is irritating so it has been used as an impregnate which is processed in a ball mill. This is then placed in a semipermeable membrane.

The mineral "ascarite" or soda lime is also used for this purpose. Chlorates, peroxides, and alkali metal superoxides absorb CO2 but generate oxygen which defeats the intended purpose of reducing the oxygen levels.

Physical absorbers including activated carbons, zeolites, silicas, aluminas, and ion exchange resins will also absorb CO2.

The CO2 absorber may be mixed with a desiccant such as a silica gel to absorb exhaled water vapor.

The oxygen absorber 62 of FIG. 6 may also be used with the carbon dioxide absorbing system of FIG. 7. This has the advantage of being able to further lower the oxygen level by increasing the relative percentage of nitrogen entering the chamber 20.

It should be appreciated that the devices shown in FIGS. 6 and 7 allow the simulation of high altitudes without requiring power compressors or other active components.

A key feature of the high-value embodiment of this invention is a breathing apparatus that may have its disposable components filled by common household materials, thus saving significant expense. Other teachings featured complex high-powered pump driven machines or very short acting chemical based systems. The CO2 scrubber chamber 70 is designed to be easily removed and refilled with calcium carbonate or sodium hydroxide (lye) and returned to the exchange chamber 20. In this way, the larger quantities of chemicals that are needed to provide a full night's operation are not prohibitively costly nor does the user have to stock canisters refills. A refill canister could require between 1 and 8 pounds of absorbent for a full night with a typical user. The oxygen scrubber chamber 62 is designed to be easily removed and refilled with steel wool moistened with vinegar and returned to the exchange chamber 20. Again, in this way, the larger quantities of chemicals that are needed to provide a full night's operation are not prohibitively costly nor does the user have to stock canisters refills.

I claim:

1. A device for acclimating an individual to high altitudes while sleeping, said device comprising:
   a mask for placement on the individual's face, said mask being arranged and configured to cover at least the individual's nose and mouth;
   said mask being soft and comfortable to avoid sleep interference;
   said mask having a securement means to maintain its position during sleeping;
   a gas exchange unit having a fluid inlet and a fluid outlet, said fluid outlet of said gas exchange unit being in bi-directional fluid communication with said mask;
   an element to retard the flow of replacement air into the gas exchange unit;
   a removable element of carbon dioxide absorbant;
   to reduce the level of oxygen contained within said gas exchange unit to simulate high altitude ambient air while the user is sleeping.

2. The device of claim 1 in which the element to absorb carbon dioxide contains lime.

3. The device of claim 1 in which the element to absorb carbon dioxide contains a metal hydroxide.

4. The device of claim 1 in which the element to absorb carbon dioxide contains a metal carbonate.

5. A device for physiologic adjustment while sleeping, said device comprising:
   a mask for placement on the individual's face, said mask being arranged and configured to cover at least the individual's nose and mouth;
   said mask being soft and comfortable to avoid sleep interference;
   said mask having a securement means to maintain its position during sleeping;
   a gas exchange unit having a fluid inlet and a fluid outlet, said fluid outlet of said gas exchange unit being in bi-directional fluid communication with said mask;
   an element to retard the flow of replacement air into the gas exchange unit;
   a removable element of carbon dioxide absorbent;
   to reduce the level of oxygen contained within said gas exchange unit to simulate high altitude ambient air while the user is sleeping.

6. The device of claim 1 in which the element to absorb carbon dioxide contains a metal hydroxide.

7. The device of claim 1 in which the element to absorb carbon dioxide contains a metal carbonate.

8. A method for simulating high altitudes while sleeping, said method including the steps of:
   placing a mask on an individual's face, said mask being arranged and configured to cover at least the individual's nose and mouth;
   connecting the mask to a gas exchange unit;
   sensing the oxygen level in the gas exchange unit;
   allowing room air into the gas exchange unit when the oxygen level is below a preset level;
   retarding the flow of room air into the gas exchange unit when the oxygen level is above a preset desired level;
   to reduce the level of oxygen contained within said gas exchange unit.

9. The method of claim 8 with the additional step of absorbing excess carbon dioxide in the gas exchange unit.

10. The method of claim 9 in which the step of absorbing excess carbon dioxide is performed at least in part with a metal hydroxide.

11. The method of claim 9 in which the step of absorbing excess carbon dioxide is performed at least in part with a metal carbonate.

12. The method of claim 8 with the additional step of converting a desired altitude setting into the desired preset oxygen level.

13. The method of claim 8 with the additional step of allowing the entrance of room air when a preset time has elapsed.

* * * * *